(12) United States Patent
 Knobloch

(10) Patent No.: US 9,278,194 B2
(45) Date of Patent: Mar. 8, 2016

(54) PROTECTIVE DEVICE FOR PROTECTING A PORT NEEDLE OR HUBER NEEDLE

(75) Inventor: Helmut Knobloch, Kreuzau (DE)

(73) Assignee: PFM MEDICAL AG, Cologne (DE)

( * ) Notice: Subject to any disclaimer, the term of this patent is extended or adjusted under 35 U.S.C. 154(b) by 76 days.

(21) Appl. No.: 13/876,215

(22) PCT Filed: Mar. 28, 2011

(86) PCT No.: PCT/EP2011/001542
§ 371 (c)(1),
(2), (4) Date: Apr. 17, 2013

(87) PCT Pub. No.: WO2012/041408
PCT Pub. Date: Apr. 5, 2012

(65) Prior Publication Data
US 2013/0218085 A1    Aug. 22, 2013

(30) Foreign Application Priority Data

Sep. 27, 2010  (DE) ............... 20 2010 013 612 U

(51) Int. Cl.
*A61M 25/02* (2006.01)
*A61M 5/158* (2006.01)
(52) U.S. Cl.
CPC ............ *A61M 25/02* (2013.01); *A61M 5/158* (2013.01); *A61M 2005/1586* (2013.01)
(58) Field of Classification Search
CPC ............ A61M 25/02; A61M 5/158; A61M 2005/1586
USPC .................. 604/174, 177, 180, 263
See application file for complete search history.

(56) References Cited

U.S. PATENT DOCUMENTS

| | | | |
|---|---|---|---|
| 3,782,377 A | 1/1974 | Rychlik | |
| 4,633,863 A | 1/1987 | Filips et al. | |
| 4,645,495 A * | 2/1987 | Vaillancourt | 604/180 |
| 4,679,553 A | 7/1987 | Proulx et al. | |
| 8,100,862 B2 * | 1/2012 | Bierman | 604/174 |
| 8,597,253 B2 * | 12/2013 | Vaillancourt | 604/174 |
| 2004/0158209 A1 | 8/2004 | Wright | |
| 2008/0200880 A1 * | 8/2008 | Kyvik et al. | 604/180 |

FOREIGN PATENT DOCUMENTS

| | | |
|---|---|---|
| DE | 37 19 238 | 12/1988 |
| DE | 37 44 527 | 7/1989 |
| WO | 2007/011596 | 1/2007 |

OTHER PUBLICATIONS

International Search Report from corresponding PCT Application No. PCT/EP2011/001542 dated Nov. 7, 2011.

* cited by examiner

*Primary Examiner* — Theodore Stigell
(74) *Attorney, Agent, or Firm* — Grossman, Tucker, Perreault & Pfleger, PLLC

(57) ABSTRACT

Protective device for protecting a port needle or Huber needle against shifting and for protecting at least one port needle puncture site and/or incision site. A frame-like spacer element is provided with an inner opening, recess or cutout for surrounding or receiving the port needle or Huber needle, which frame-like spacer element has a height corresponding to at least half the height of the port needle or Huber needle and has at least one means for fixing or securing the spacer element in the area of a port.

17 Claims, 4 Drawing Sheets

PROTECTIVE DEVICE FOR PROTECTING A PORT NEEDLE OR HUBER NEEDLE

CROSS REFERENCE TO RELATED APPLICATIONS

This is the U.S. National Phase application under 35 U.S.C §371 of International Patent Application No. PCT/EP2011/ 001542 filed Mar. 28, 2011, which designated the United States, which claims the benefit of German Patent Application No. 20 2010 013 612.1 filed on Sep. 27, 2010, both of them are incorporated by reference herein.

FIELD OF THE INVENTION

The invention relates to a protective device for protecting a port needle or Huber needle against shifting and for protecting at least one port needle puncture site and/or incision site.

BACKGROUND

Port catheters and port needles are known in the prior art. Port catheters are fixedly implanted subcutaneous plastic reservoirs connected to the central venous system in order to permit a reliable vascular access. A port catheter is applied when long-term or frequent vascular access is required. The port is usually composed of a chamber with a thick silicone membrane and an attached tube or catheter. After implantation of the port catheter, the access to the blood stream of the patient can be established by percutaneous insertion of what is called a port needle or Huber needle through the silicone membrane. The port needle lying in the chamber allows blood to be removed or allows a medicament to be administered by infusion. After application of the port needle, that is to say after the latter has been inserted into the silicone membrane of the port, and if the injection is intended to last a considerable time, the port needle is usually fixed in place with a sterile plaster in order to avoid shifting of the port needle or Huber needle. The port needle is usually changed after at most eight days, in order to avoid infections. After the port needle has been removed, the injection site is usually disinfected and covered with a sterile plaster. Port systems are known from DE 37 44 527 A1 or DE 37 19 238 A1, for example.

SUMMARY

Port needles or Huber needles are known in various design variants. There are in particular also safety arrangements for avoiding the risk of needle-stick injuries when pulling the port needle or Huber needle. Huber needles are port needles with a very specific ground tip, the Huber tip.

When port needles that are to remain in place for long periods are fixed by plasters in order to protect them against shifting, the needle may in fact shift even as the plaster is being applied. Moreover, such a plaster is not able to protect against shifting in every case, and it would therefore be desirable here to provide a more reliable means of protecting against shifting of the port needle or Huber needle.

The object of the present invention is therefore to make available a protective device for protecting a port needle or Huber needle against shifting, which device permits more reliable protection against shifting of the port needle or Huber needle than is possible with a conventional plaster.

The object is achieved, as to a protective device for protecting a port needle or Huber needle against shifting and for protecting at least one port needle puncture site and/or incision site, by the fact that a frame-like spacer element is provided with an inner opening, recess or cutout for surrounding or receiving the port needle or Huber needle, which frame-like spacer element has a height corresponding to at least half the height of the port needle or Huber needle and has at least one means for fixing or securing the spacer element in the area of a port. For a protective device for protecting a port needle or Huber needle against shifting, the object is achieved by the fact that at least one base element, having an inner opening for receiving at least part of the port needle or Huber needle, and at least one cover element, which can be arranged above the base element, are provided, wherein the base element has at least one means for fixing the position on the skin of a patient, and the cover element has a means for fixing the port needle or Huber needle relative to the base element. Developments of the invention are defined in the dependent claims.

In this way, a protective device for protecting a port needle or Huber needle against shifting is made available which permits particularly good fixing of the position of the port needle or Huber needle, since that part of the port needle or Huber needle that lies on the surface of the skin of the patient, and that is hereinafter referred to as the upper part, is received in the inner opening of the protective device. The frame-like spacer element surrounds this part of the port needle or Huber needle lying on the surface of the skin of the patient and extends over a large part of the height of the needle. In this way, a kind of embankment is created which provides protection all the way round the port needle or Huber needle.

At least one cover means, in particular a cover film, such as a plaster or another film element, can be provided for sealingly covering the frame-like spacer element. This advantageously has the adhesive layer for securing to the upper face of the protective device for the port needle or Huber needle. It is in this way possible to completely seal the space which forms in the frame-like spacer element and in which the port needle or Huber needle is arranged. Protection against entry of bacteria and contaminants is thereby provided. Specifically in the case of long dwell times of the port needle or Huber needle, this provides optimal hygiene for avoiding infections.

The frame-like spacer element can be in one part, two parts or even multiple parts. In the two-part or multi-part design, it is particularly easy to position the protective device around the port needle only after the port needle has been applied, that is to say after the port chamber or silicone membrane has been punctured. When a two-part frame-like spacer element is provided, these two parts can be arranged one after the other in the area of the port needle puncture site or the incision site where the port was implanted. Thus, after the port has been punctured with the port needle, the entire port area can be surrounded by the frame-like spacer element, or the two parts thereof, and then covered by the at least one cover means.

In the case of a one-part design, it is possible to design the frame-like spacer element already like a hood, i.e. to provide a recess for receiving the port needle or Huber needle. The then hood-like spacer element is thus designed like a cushion and mostly in one part and from one material. The hood-like (frame-like) spacer element permits covering and sealing of the entire port needle or Huber needle, which can additionally be covered by the at least one cover means. The cover means in this case advantageously has a greater dimension than the frame-like spacer element, in order to permit a further seal, all the way round the spacer element, when the latter has been attached and affixed to the skin of a patient. The cover means can be formed integrally with the frame-like spacer element or can be firmly connected thereto. In the case of the integral design, the material of the frame-like spacer element can be made thin like a film in the circumferential edge area (in contrast to the embankment-like design for protecting the port needle or Huber needle) in order to improve the flexibility for affixing or attaching to the skin of a patient.

When a frame-like spacer element in one part is provided, it has proven very advantageous for the cover means and/or the frame-like spacer element to be partially slit in the edge area. A catheter of the port needle or Huber needle, or an attachment piece for such a catheter, can be guided through such a slit and, correspondingly, removed from the protective device in order to provide accessibility. After the attachment piece or the catheter has been guided through, the slit can be closed, when affixing the protective device to the skin of the patient, by allowing the slit-forming edges of the frame-like spacer element and of the cover means to abut one another. The slit or gap is thereby closed and thus no longer exists, such that the port needle or Huber needle is completely sealed all the way round.

The means for fixing or securing the spacer element to the skin of the patient can be an adhesive layer, which is arranged on the underside of the spacer element or on the underside of a support element on which the spacer element is or can be mounted. The spacer element can thus be affixed directly to the skin of the patient, or the spacer element is mounted on a support material which is in turn fixed to the skin of the patient, in particular by adhesion.

The inner opening, recess or cutout in the frame-like spacer element is advantageously dimensioned such that a base plate of the port needle can be received therein. Port needles often have what are called base plates which, particularly when safety means are provided for avoiding needle-stick injuries when pulling the port needles, are positioned to be gripped and held securely on the surface of the skin of the patient. The inner opening of the frame-like spacer element can be dimensioned such that the base plate of the port needle or Huber needle is received optimally therein. Moreover, it is likewise possible for the dimensions of the inner opening, recess or cutout to be adapted to that part of the port needle or Huber needle which, during use of the protective device, is or can be arranged in the opening, recess or cutout. The opening, recess or cutout can taper conically in particular, such that, in the outer area, which is arranged away from the skin of the patient, there is a smaller dimension of the inner opening, recess or cutout than in the area where the spacer element rests on the skin surface of the patient. In the tapered area of the inner opening, recess or cutout, the latter can be adapted to the corresponding dimensions of the port needle in the area surrounded by the inner opening, recess or cutout. The danger of dirt and bacteria gaining entry can be minimized by the provision of this smaller dimension of the inner opening, recess or cutout in the outer area. There then remains only a small area that is covered by the cover means, in particular cover film, for sealing the port system.

The frame-like spacer element is advantageously made of a material that takes up or absorbs liquid. In particular, the spacer element can be gel-like, being made in particular of a glycerol gel material. By means of the ability to take up liquid, it is possible for emerging secretions to be taken up by the protective device directly and for the port needle puncture site to be kept dry in this way. It is also possible in this way to avoid complications resulting from the port needle puncture.

The effect of the gel material is based on its physical property. The fact that glycerol, as polyvalent alcohol, has a very good binding capacity for water means that germs, bacteria and/or fungi present on the skin of a patient are removed from the culture medium, and no growth of these takes place. The pH is also reduced, although this is relevant only with correct wound healing. Since the gel has no sponge effect, i.e. the liquid taken up also remains in the gel and cannot, as in a sponge, escape again by pressure, this also ensures that germs do not escape during the wearing time, for example when confined to bed or as a result of other mechanical loads.

The frame-like spacer element can be profiled and/or have incisions or folding aids, particularly in one or more corner areas. When a frame-like spacer element in one part is provided and has been arranged over the port needle or Huber needle, it can be folded in at the predetermined locations, particularly at the corners, and thus adapted to the outer dimensions of the port needle or Huber needle and, if appropriate, to the base plate thereof.

The port needle or Huber needle can thus be fixed particularly firmly in position and protected against unwanted movement.

It has also proven advantageous to provide a transfer film element which is or can be arranged detachably and removably on that surface of the protective device or of a support substrate lying opposite the fixing or securing means. The transfer film element can have reinforced edge areas. By provision of such a transfer film element, it is possible, before the protective device is applied to the skin of a patient, to protect the upper side of the protective device against damage and then to considerably facilitate application to the skin in the area of the port needle or Huber needle, since the transfer film element can be very firmly gripped during positioning without directly touching the surface of the protective device or in particular of the frame-like spacer element. This proves particularly advantageous specifically when a frame-like spacer element in one part is provided, since the latter can first of all be optimally positioned, and only thereafter is the transfer film element removed.

If the port needle or Huber needle is to be fitted only for quite a short time, it is sufficient to provide, instead of the frame-like spacer element, a base element having an inner opening for receiving at least part of the port needle or Huber needle. This base element is fixed in position on the skin surface of the patient, particularly by provision of an adhesive means. For example, it can cover a base plate of the port needle, such that only a narrow and if appropriate wing-shaped part of the port needle or Huber needle passes through the inner opening of the base element. For further fixing, and at the same time also for further protection of the port needle or Huber needle against shifting, the base element is covered by a cover element. The latter has in particular an adhesive means for fixing the cover element both to the surface of the base element and also to the port needle or Huber needle. The cover element is advantageously designed and dimensioned such that the port needle or Huber needle is covered substantially completely. The cover element can be partially slit in the edge area, so as to permit adaptation to the shape of that part of the port needle or Huber needle protruding on the outside of the base element, through the inner opening thereof, and complete sealing.

The base element can be designed such that a fixing or adhesive means for affixing to the skin of the patient is provided only on two mutually opposite sides thereof.

The base element, at least in the area where the inner opening is provided for engagement over part of the port needle or Huber needle, is advantageously made of a more stable material than in the area away from this, that is to say the area distant from the port needle puncturing site, particularly the area of the base element having the fixing means, e.g. adhesive means. This permits very good fixing of the position and, at the same time, a certain degree of hold against shifting of the port needle.

BRIEF DESCRIPTION OF THE DRAWINGS

For a more detailed explanation of the invention, illustrative embodiments thereof are described in more detail below with reference to the drawings, in which.

DETAILED DESCRIPTION

Figure 1:
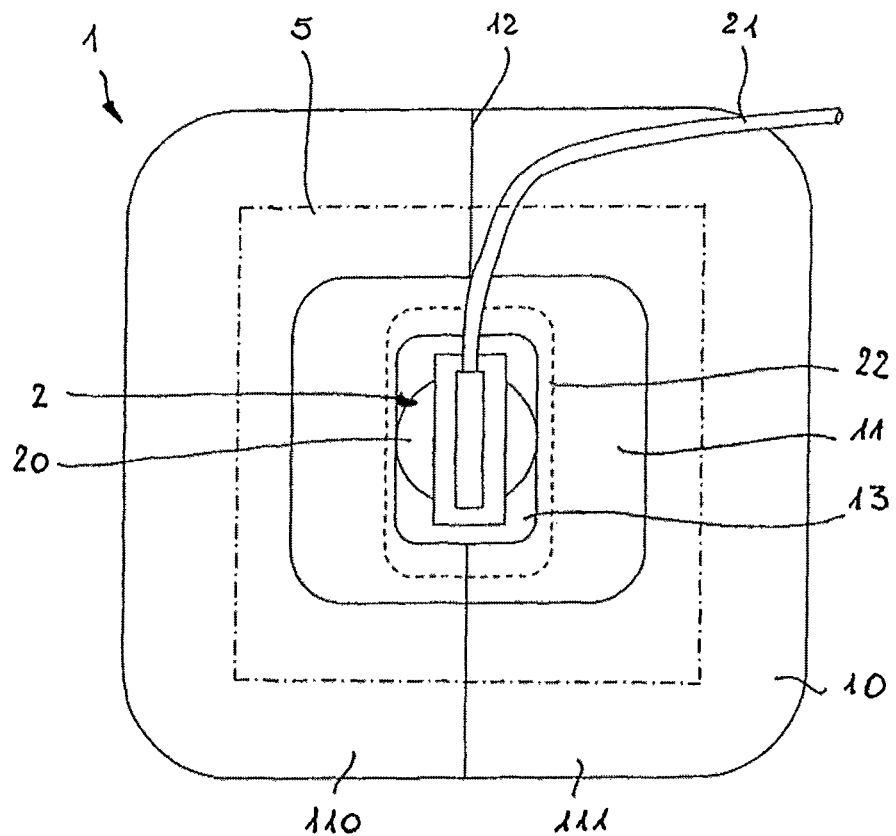
FIG. 1 shows a plan view of a first embodiment of a protective device according to the invention.

FIG. 1 shows a plan view of a protective device 1 for protecting a port needle 2 against shifting. In the embodiment shown in FIG. 1, the protective device 1 has a support element 10 and a frame-like spacer element 11. The frame-like spacer element 11 and the support element 10 are designed in two parts, as is indicated by the connecting line 12 in FIG. 1. It is possible in principle for the frame-like spacer element and the support element to be designed in one part, or even in more than two parts. By providing the support element and frame-like spacer element in two or more parts, the protective device 1 can be applied particularly easily and with precise positioning around a port needle puncture site 40.

In the embodiment according to FIG. 1, an upper part 20 of the port needle or Huber needle is received in an inner opening 13, which is formed by the frame-like spacer element 11 or by the two joined halves 110, 111 of the frame-like spacer element 11. By providing a frame-like spacer element in two parts, it is particularly easy, after insertion of the port needle, that is to say after insertion thereof into the port 3, as can be seen in FIG. 2, to position the protective device and receive the upper part 20 of the port needle 2 in the inner opening 13 of the spacer element.

As is shown in FIG. 1, the inner opening 13 can receive only the upper part 20 of the port needle 2 and thus have very small dimensions. In an alternative embodiment, as can be seen in cross section in FIG. 2, the inner opening 13 of the two-part or multi-part or even one-part frame-like spacer element 11 can have dimensions slightly smaller than the dimensions of a base plate 22 of the port needle 2. In this way, the port needle is fixed in the area of the base plate 22 thereof, but the dimensions of the inner opening 13 are greater than in the embodiment according to FIG. 1, in which only the upper part 20 of the port needle is received in the opening and fixed above this.

Figure 2:
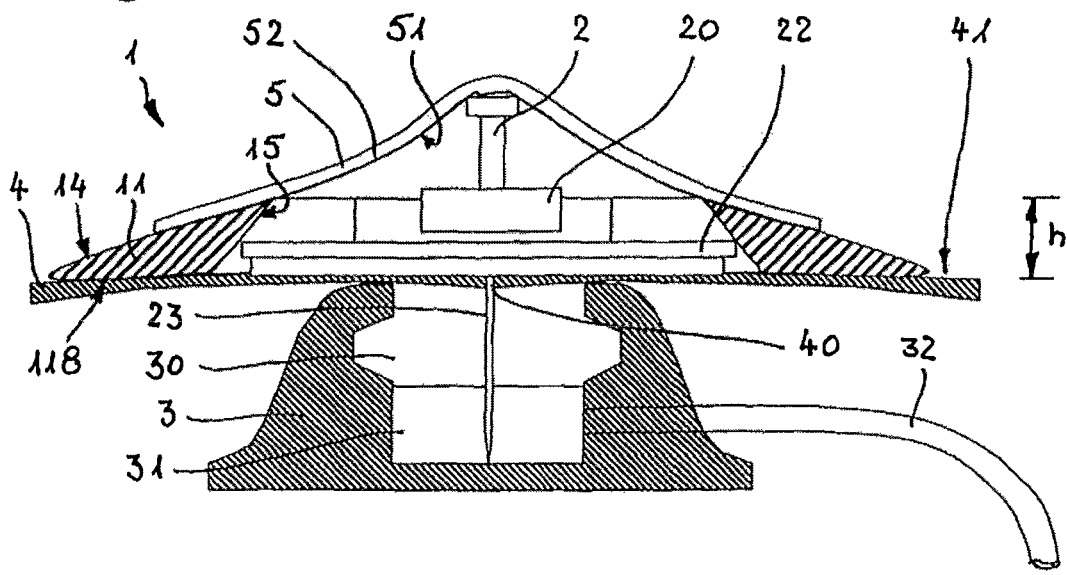
FIG. 2 shows a cross-sectional view of a second embodiment of a protective device according to the invention.

As can be seen particularly clearly from the cross-sectional view in FIG. 2, the frame-like spacer element 11 has a shape similar to an embankment or dike, in other words has oblique outer wall flanks 14 in the outwardly directed area and, in order to delimit the inner opening 13, also has an obliquely tapering wall 15. The base plate 22 is supported and held in its position by the obliquely tapering wall 15 as soon as a transverse force is applied to the port needle. In the embodiment according to FIG. 1, the port needle is accordingly held in the area of the upper part 20 thereof. The approximately rectangular opening 13 shown in FIG. 1 can also be completely square or adapted to the dimensions and shape of the upper part 20 of the port needle.

As can be seen particularly clearly from the cross-sectional view in FIG. 2, the frame-like spacer element 11, in its height direction h, extends along much of the height of the port needle in the area of the base plate thereof and of the upper part thereof. In this way, when transverse forces occur, a particularly secure and firm hold of the port needle is possible in order to avoid shifting.

The frame-like spacer element 11 lies on the skin 4 of the patient either via its support element 10, as can be seen in FIG. 1, or directly, as is shown in FIG. 2. FIG. 2 also shows the puncture site 40 of the needle 23 of the port needle 2. The latter is likewise inserted into the port 3, passing through the silicone membrane 30 of the latter and projecting into an inner chamber or port chamber 31. A catheter 32, which allows connection to a blood vessel of the patient, is likewise connected to this port chamber 31. As is also indicated in FIG. 1, the port needle is provided with a tube 21, which allows a medicament to be administered or blood to be removed.

Both the protective device 1 according to FIG. 1 and also the protective device according to FIG. 2 can, after said protective device has been positioned over the port needle, be covered with a cover element 5, in particular a plaster-like film, and protected against entry of dirt and bacteria. Such a cover element 5 is accordingly indicated in FIGS. 1 and 2.

The frame-like spacer element 11 can be made of a material that absorbs liquid, in particular of a gel, for example a glycerol gel. In this way it is possible for secretions emerging at the puncture site 40 to be taken up directly, such that inflammations and infections can be better avoided in this way.

Figure 3:
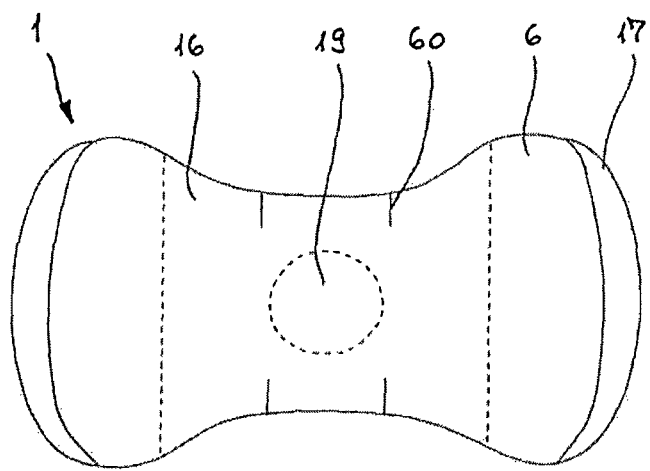
FIG. 3 shows a plan view of a third embodiment of a protective device according to the invention.
Figure 4:
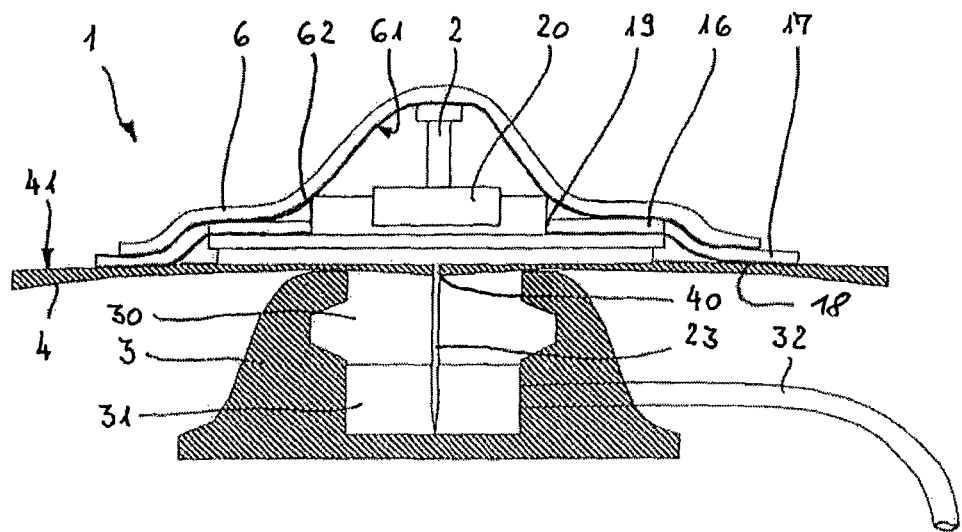
FIG. 4 shows a cross-sectional view of the protective device according to FIG. 3.

FIGS. 3 and 4 show another embodiment of the protective device 1. The latter serves to fix the port needle or Huber needle in order to protect the latter against shifting. This design variant of the protective device 1 is provided for a short dwell time of the port needle in the port 3, whereas the design variants according to FIGS. 1 and 2 are provided for a longer dwell time of the port needle. In the embodiment according to FIGS. 3 and 4, the protective device 1 has a base element 16, which is thinner than the frame-like spacer element 11. However, the base element 16 advantageously has sufficient stability to still allow the port needle to be fixed in position.

To secure the protective device or the base element 16 on the surface 41 of the skin 4 of the patient, said base element 16 has, at its ends, securing elements 17 which, on the one hand, have greater flexibility and possibly elasticity than the base element 16 and, on the other hand, are provided on one surface with an adhesive layer 18. With the latter, they are affixed to the skin surface 41. Before the use of the protective device, the adhesive layer 18 can be provided with a protective film in order to avoid its adhering too early.

The support element 10 and the skin-facing underside of the frame-like spacer element 11 according to FIGS. 1 and 2 are also each provided with a corresponding adhesive layer 118, allowing them to be affixed to the skin surface 41.

As is also already the case in the design variant of the protective device 1 according to FIGS. 1 and 2, an inner opening 19 is also formed in the embodiment according to FIGS. 3 and 4, which inner opening 19 receives the upper part 20 of the port needle 2. This can be seen particularly in FIG. 4.

Therefore, in this design variant too, the port needle 2 is first inserted into the port 3, and only thereafter is the protective device 1 positioned over the port needle 2. Since the protective device 1 in this design variant is in one part, with respect to the base element, it is threaded over the tube 21, with the tube 21 engaging in the inner opening 19, advanced as far as the upper part 20 of the port needle and then fixed on the skin surface 41.

In this design variant too, after the protective device 1 has been affixed or secured to the skin surface 41, the puncture site 40 is protected against entry of dirt and bacteria by means of a cover element 6 being positioned over the base element 16 and the port needle 2. In this case, in order to permit a particularly good fit to the shape of the port needle, the cover element 6 has outer slits 60. Corresponding slits can also be provided for the passage of the tube 21. However, this is not shown in FIGS. 3 and 4.

The cover element 6, like the cover element 5, can also be provided on the underside thereof with an adhesive layer 62, as the cover element 5 is provided with an adhesive layer 52. This permits precise positioning and securing of the respective cover element 5, 6 on the outside of port needle and frame-like spacer element or support element or base element.

Figure 5:
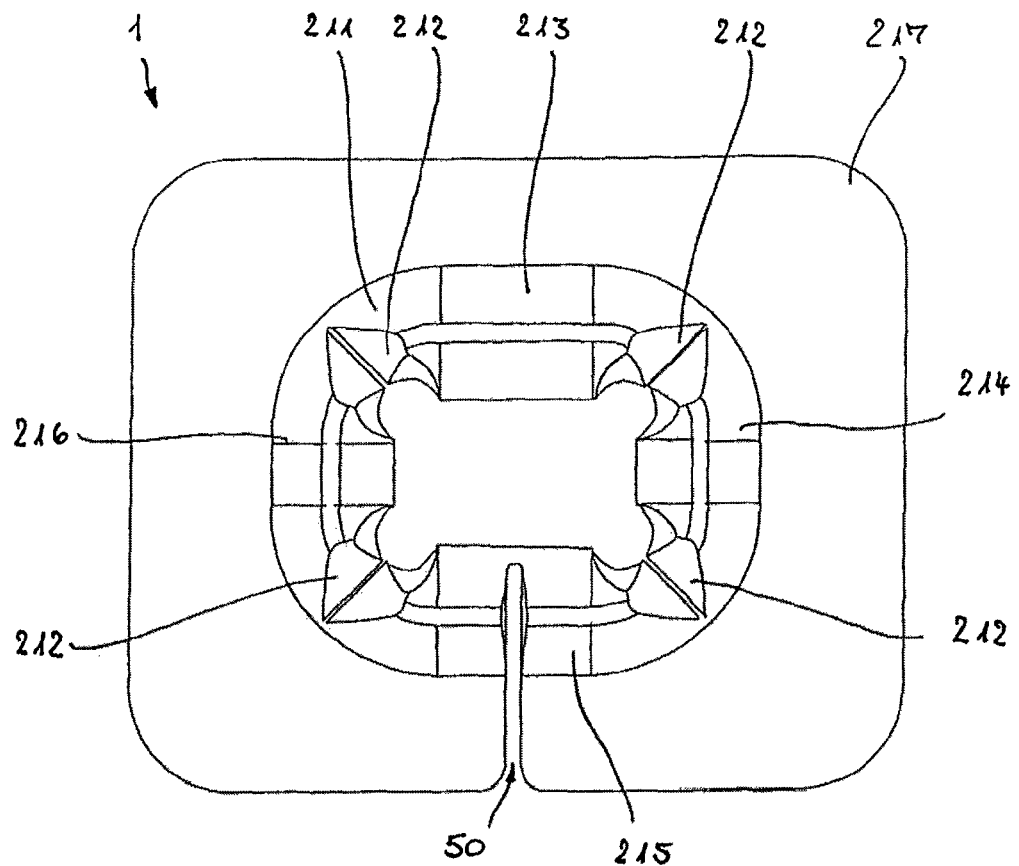
FIG. 5 shows a plan view of another embodiment of a protective device according to the invention.

FIG. 5 shows a one-part embodiment of the protective device 1. In this case, as can be better seen from FIG. 6, a hood-shaped frame-like spacer element 211 is provided. The latter can therefore completely cover the port needle or Huber needle 2, as is indicated in FIG. 7.

To permit simple and optimal positioning of the spacer element 211 over the port needle 2, the spacer element 211 is profiled or is provided with a number of incisions 212. These are arranged particularly in the corners of the frame-like spacer element 211. The provision of the incisions 212 means that, despite the one-part design of the frame-like and hood-like spacer element 211, the latter can first be positioned over the port needle 2, and only thereafter are the side walls 213, 214, 215, 216 of the frame-like spacer element 211 folded down in the direction of the skin of the patient, whereupon mutually adjoining walls, which have the incisions 212 or notches between them, are then positioned closer to each other by folding the walls towards each other in the area of the incisions.

Figure 6:
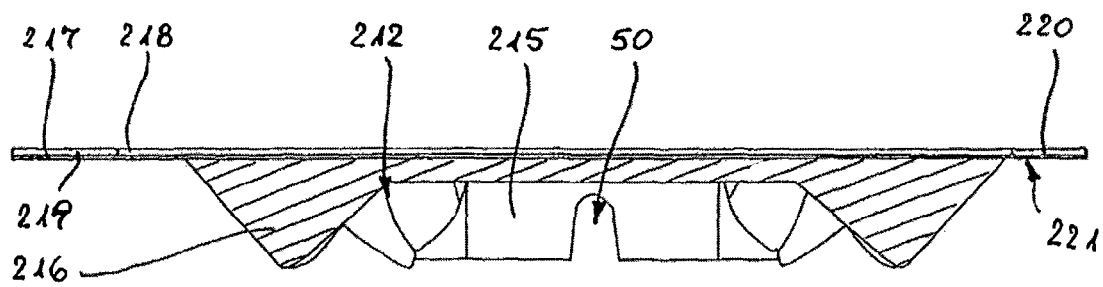
FIG. 6 shows a cross-sectional view of the protective device according to FIG. 5.
Figure 7:
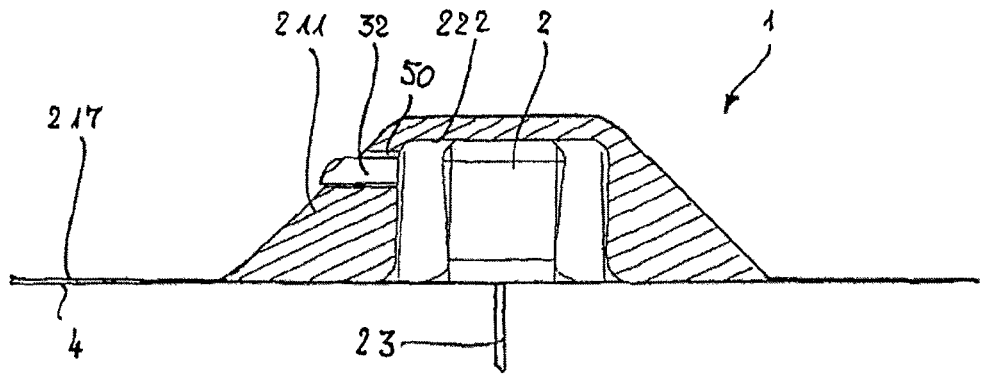
FIG. 7 shows a cross-sectional view of the protective device according to FIG. 5 when arranged over a port needle.

As can be seen particularly clearly from FIGS. 5 and 6, the hood-shaped, frame-like spacer element 211 is arranged on a support substrate 217. The latter is covered, on its upper face, with a transfer film element 218. The transfer film element has reinforced edges 219, 220 at its ends. These edges serve for easier removal after the protective device has been fully positioned on the skin of a patient. The underside of the support substrate 217 is provided with an adhesive layer 221. A layer having another adherence action can also be provided here.

The support substrate can be formed in one piece with the hood-shaped, frame-like spacer element 211, or can be separate from the latter and connected firmly thereto. In the one-piece design, the support substrate is made, for example, of a gel material, likewise the spacer element 211. In the case of a multi-part design with connection of the support substrate to the hood-shaped, frame-like spacer element 211, the support substrate can be made of any other desired suitable material that has sufficient flexibility to adapt as closely as possible to the skin surface when applied thereto.

Like the support substrate 217, the hood-shaped, frame-like spacer element 211 has a slit 50 in the edge area. This slit 50 serves for insertion of the catheter 32, so as to be able to guide the latter out through the protective device. After the catheter has been guided out, the slit 50 is closed when the protective device is affixed to the skin of the patient, as can be seen particularly from the third view in FIG. 8. This permits tight sealing of the site where the catheter 32 is guided out from the interior of the protective device.

Figure 8:
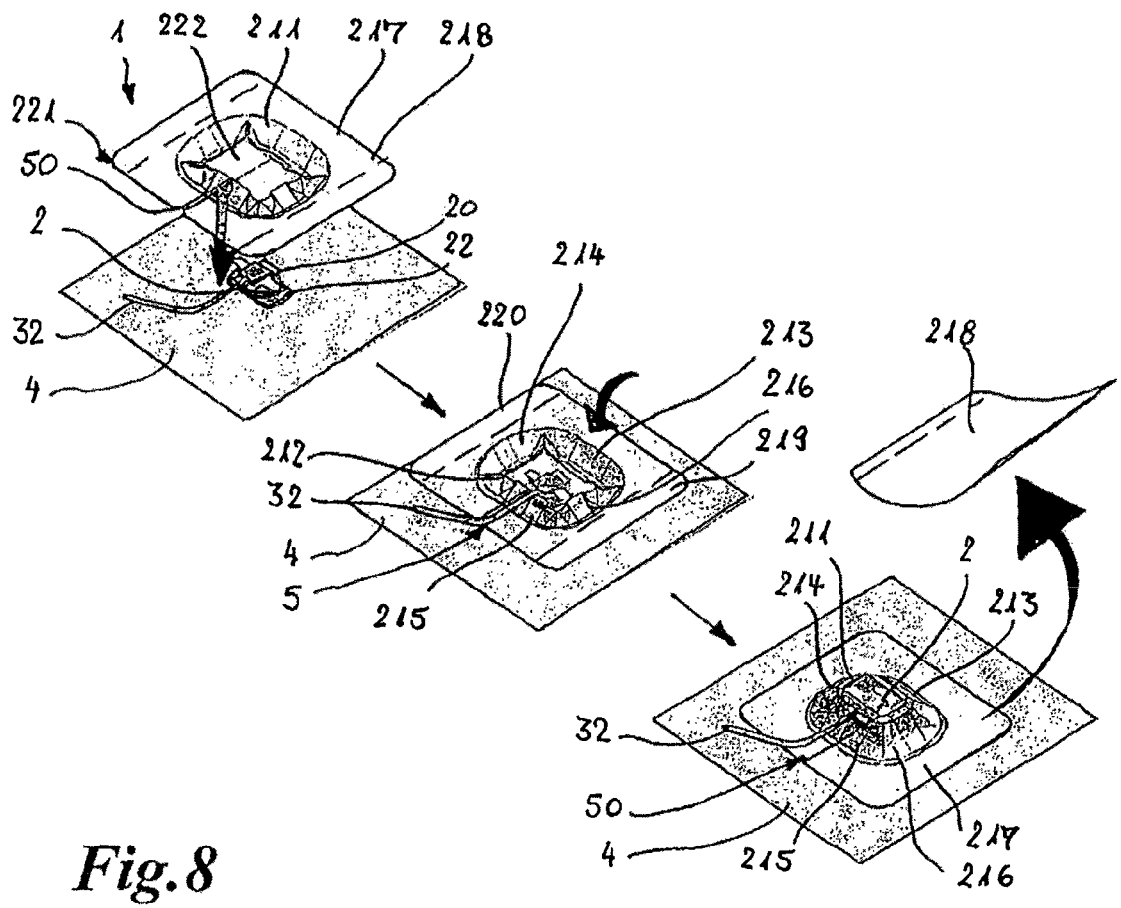
FIG. 8 shows perspective views of the individual steps involved in arranging the protective device according to FIG. 5 over an inserted port needle.

FIG. 6 shows a cross-sectional view of the frame-like or hood-like spacer element 211 before the final positioning over the port needle 2, whereas FIG. 7 shows the arrangement after final positioning of the port needle 2. FIG. 8 shows the sequence involved in positioning the hood-like or frame-like spacer element 211 over the port needle 2, which is already positioned on the skin of the patient.

As can be seen from the first view in FIG. 8, the port needle 2 with the catheter 32 is first positioned on the skin of the patient after insertion of the needle into the port 3 (not shown). The protective device is arranged over the port needle 2, and an inner recess 222 of the spacer element 211 receives the port needle. As the protective device is lowered onto the port needle, the catheter 32 passes through the slit 50, and the port needle itself is arranged with its upper part 20 and its base plate 22 in the inner recess 222 of the spacer element. The side walls 213 to 216 of the hood-shaped, frame-like spacer element 211 are then lowered or pressed down, all around the port needle, in the direction of the skin 4 of the patient. The incisions 212 or notches arranged in the corners in this case allow the side walls 213 to 216 to be positioned as close as possible to the port needle. By applying a pressure force both to the side walls and also to the support substrate 217, the latter too can then be attached to the patient's skin 4 and, by virtue of the presence of the adhesive layer 221, affixed thereto. After the protective device has been completely positioned and affixed, the transfer film element 218 can be gripped at its reinforced edges 219, 220 and peeled off from the upper face of the support substrate 217. This is indicated in the third view in FIG. 8.

After the protective device has been completely applied, engaging over the port needle 2, the arrangement shown in FIG. 7 is obtained, in which the port needle is engaged and supported on all sides by the side walls 213 to 216 of the spacer element 211.

In addition to the above-described design variants, shown in the figures, of protective devices for protecting a port needle or Huber needle against shifting, many others can also be formed in which a frame-like spacer element is provided which has an inner opening for surrounding the port needle and which has a height corresponding to at least half the height of the port needle or Huber needle and has at least one means for fixing or securing the spacer element in the area of a port. Alternatively, at least one base element, having an inner opening for receiving at least part of the port needle or Huber needle, and at least one cover element, which can be arranged over this base element, are provided, in which case both the base element and also the cover element are provided in particular with an adhesive layer or a fixing layer.

LIST OF REFERENCE SIGNS

1 protective device
2 port needle
3 port
4 skin
5 cover element
6 cover element
10 support element
11 frame-like spacer element
12 connecting line
13 inner opening
14 oblique wall flank
15 obliquely tapering wall
16 base element 17 securing element
18 adhesive layer
19 inner opening
20 upper part
21 tube
22 base plate
23 needle
30 silicone membrane
31 port chamber
32 catheter
40 puncture site
41 skin surface
50 slit
51 underside
52 adhesive layer
60 slit
61 underside
62 adhesive layer
110 half of the frame-like spacer element
111 half of the frame-like spacer element
118 adhesive layer
211 hood-shaped, frame-like spacer element
212 incision
213 side wall
214 side wall
215 side wall
216 side wall
217 support substrate
218 transfer film element
219 reinforced edge
220 reinforced edge
221 adhesive layer
222 inner recess
h height of the frame-like spacer element

The invention claimed is:

1. A medical device comprising:
   a protective device configured to protect a port needle or Huber needle receivable therein against shifting and configured to protect at least one port needle or Huber needle puncture site and/or at least one port needle or Huber needle incision site, wherein the port needle or Huber needle receivable in the protective device has a height, the protective device comprising
   a frame-like spacer element having an inner opening, recess or cutout configured to surround or receive the port needle or Huber needle, the frame-like spacer element having a height corresponding to at least half the height of the port needle or Huber needle;
   at least one cover element which sealingly covers the frame-like spacer element;
   at least one fixing or securing means configured to fix or secure the spacer element to the port needle or Huber needle and to skin of a patient;
   wherein the spacer element is in one part; and
   wherein the inner opening, recess or cutout of the frame-like spacer element comprises a through-hole oriented such that the port needle or Huber needle is receivable in the through-hole when the spacer element is fixed or secured to the patient.

2. The device according to claim 1, wherein the cover element is formed integrally with the frame-like spacer element or is firmly connected thereto.

3. The device according to claim 1, wherein the spacer element is made of a material that takes up or absorbs liquid.

4. The device according to claim 1, wherein the spacer element is a material that absorbs liquid.

5. The device according to claim 1, wherein the frame-like spacer element is profiled and/or has incisions or folding aids.

6. The device according to claim 1, wherein the fixing or securing means is an adhesive layer on the underside of the spacer element or of a support element on which the spacer element is or can be mounted.

7. The device according to claim 1, wherein a transfer film element is provided which is or can be arranged detachably and removably on a surface of the protective device or of a support substrate lying opposite the fixing or securing means, and wherein the transfer film element has reinforced edge areas.

8. The device according to claim 1, wherein the inner opening, recess or cutout in the frame-like spacer element is dimensioned such that the base plate of the port needle can be received therein.

9. The device according to claim 1, wherein the dimensions of the inner opening, recess or cutout in the frame-like spacer element are adapted to a part of the port needle which, during use of the protective device, is or can be arranged in the opening, recess or cutout.

10. The device according to claim 1, wherein the frame-like spacer element is profiled and/or has incisions or folding aids in one or more corner areas.

11. The device of claim 1, wherein the cover element is a cover film.

12. A medical device comprising:
    a protective device configured to protect a port needle or Huber needle receivable therein against shifting, comprising
       at least one base element, having an inner opening configured to receive at least part of the port needle or Huber needle;
       at least one cover element, arrangeable over the base element;
       wherein the base element has at least one fixing means configured to fix a position of the base element on skin of a patient;
       wherein the cover element has at least one fixing means configured to fix the port needle or Huber needle relative to the base element; and
       wherein the inner opening of the base element comprises a through-hole orientated such that the port needle or Huber needle is receivable in the through-hole when the base element is fixed to the patient.

13. The device according to claim 12, wherein the cover element is designed and dimensioned in such a way that the port needle or Huber needle can be covered substantially completely.

14. The device according to claim 12, wherein the cover element and/or the frame-like spacer element are partially slit in an edge thereof.

15. The device according to claim 12, wherein the base element has the fixing means on two mutually opposite sides.

16. The device according to claim 12, wherein the base element, at least in an area of the inner opening, is made of a more stable material than in an area away from the inner opening.

17. The device according to claim 12, wherein the base element, at least in an area of the inner opening, is made of a more stable material than in an area away from the inner opening in the area of the fixing or adhesive means.

* * * * *